US006890341B2

(12) United States Patent
Dieck et al.

(10) Patent No.: US 6,890,341 B2
(45) Date of Patent: *May 10, 2005

(54) METHODS AND DEVICES FOR FILTERING FLUID FLOW THROUGH A BODY STRUCTURE

(75) Inventors: Martin S. Dieck, Cupertino, CA (US); Brian B. Martin, Boulder Creek, CA (US)

(73) Assignee: Concentric Medical, Inc., Mountain View, CA (US)

( * ) Notice: Subject to any disclaimer, the term of this patent is extended or adjusted under 35 U.S.C. 154(b) by 198 days.

This patent is subject to a terminal disclaimer.

(21) Appl. No.: 10/163,155

(22) Filed: Jun. 4, 2002

(65) Prior Publication Data

US 2003/0023264 A1 Jan. 30, 2003

Related U.S. Application Data

(63) Continuation of application No. 09/434,585, filed on Nov. 4, 1999, now Pat. No. 6,425,909.

(51) Int. Cl.[7] .............................................. A61M 29/00
(52) U.S. Cl. ...................................................... 606/200
(58) Field of Search .................................. 606/200, 191, 606/192, 194, 195, 198, 189; 604/96.01; 608/189; 623/1.1–1.23

(56) References Cited

U.S. PATENT DOCUMENTS

| 5,545,214 | A | | 8/1996 | Stevens | |
|---|---|---|---|---|---|
| 5,814,064 | A | * | 9/1998 | Daniel et al. | 606/200 |
| 5,947,995 | A | * | 9/1999 | Samuels | 606/200 |
| 6,042,598 | A | * | 3/2000 | Tsugita et al. | 606/200 |
| 6,152,946 | A | * | 11/2000 | Broome et al. | 606/200 |
| 6,468,300 | B1 | * | 10/2002 | Freidberg | 623/1.13 |

FOREIGN PATENT DOCUMENTS

WO   WO 98/33443   8/1998

* cited by examiner

*Primary Examiner*—Vy Q. Bui
(74) *Attorney, Agent, or Firm*—Jens E. Hoekendjik

(57) ABSTRACT

An intravascular filter having a filament which expands a filter element. The filament is a coil which is stretched to reduce the diameter of the coil for introduction. The filter element is preferably biased toward the closed position and is opened by the coil when tension is released on the coil. The filament slides along the internal surface of the filter element so that the filter element may assume intermediate positions.

8 Claims, 6 Drawing Sheets

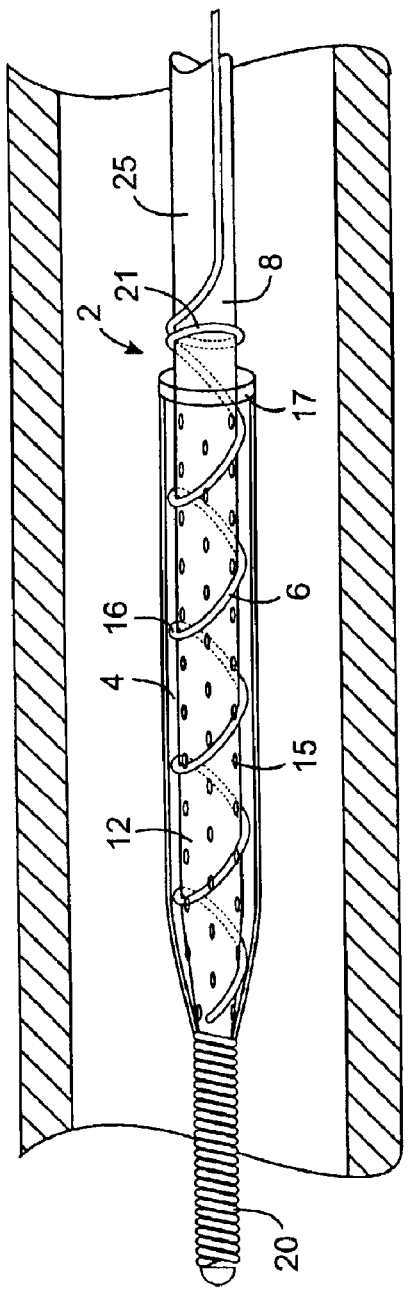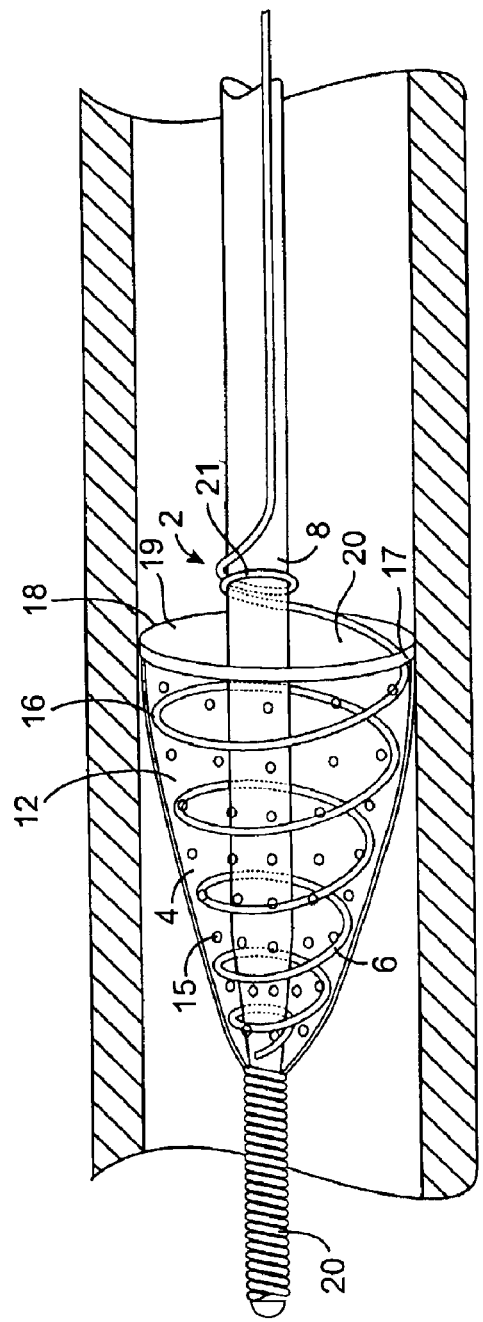

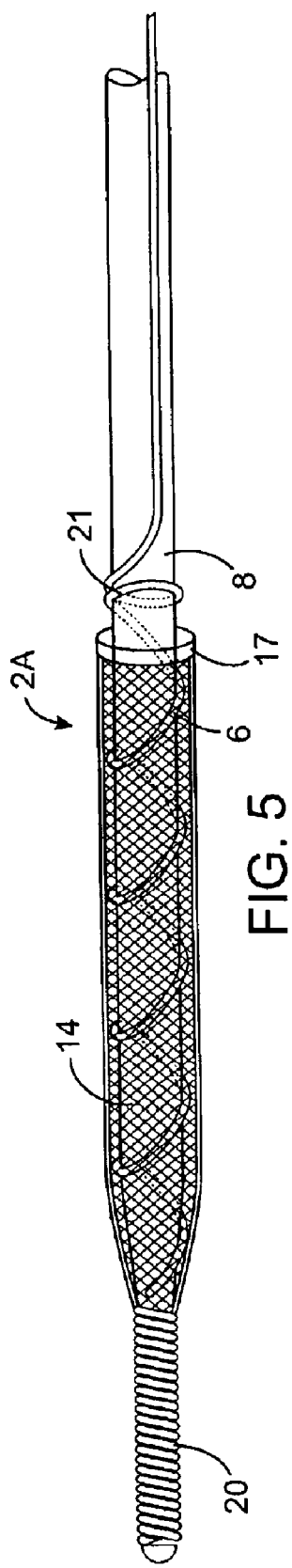
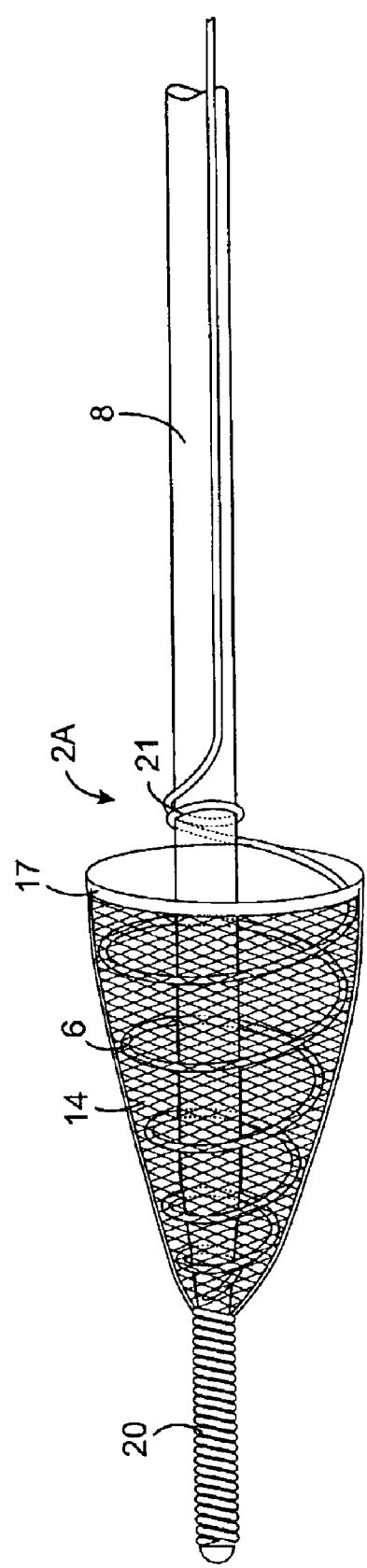

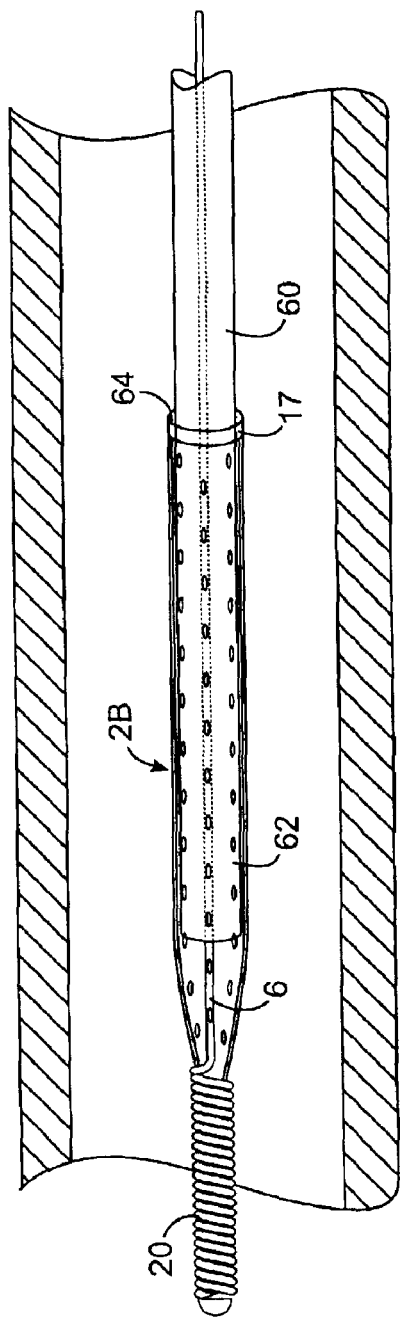
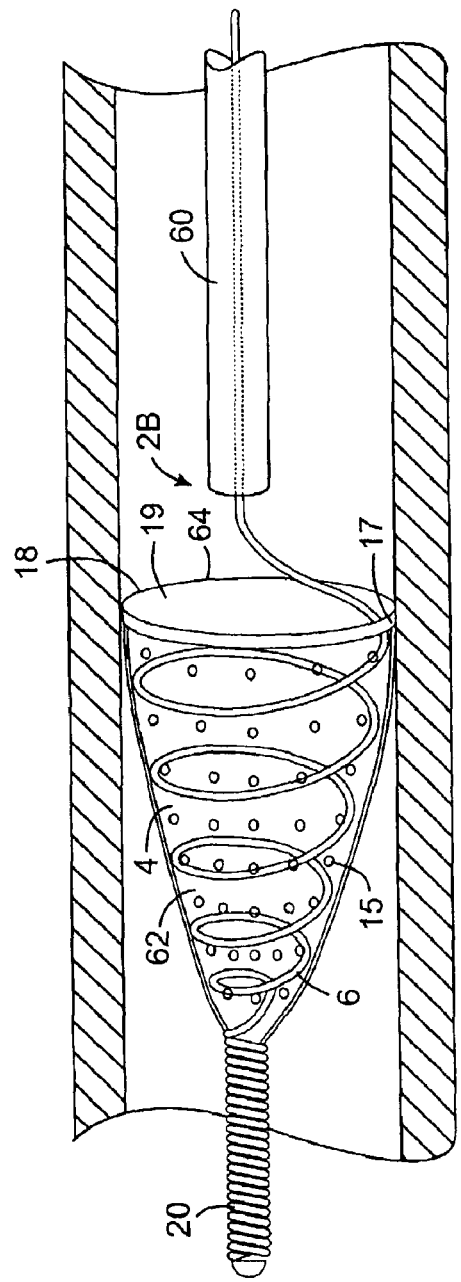
FIG. 9
FIG. 10

METHODS AND DEVICES FOR FILTERING FLUID FLOW THROUGH A BODY STRUCTURE

This is a continuation application of Ser. No. 09/434,585 file date Oct. 4, 1999 now issued as U.S. Pat. No. 6,425,909.

BACKGROUND OF THE INVENTION

The present invention is directed to methods and devices for filtering fluid flow through body structures. Such devices are used in various parts of the body, such as the vascular system, to filter out unwanted material.

Filters are used in the vascular system to remove plaque and other material which can obstruct blood vessels. Vascular filtering devices may be used during other procedures such angioplasty, stenting, endarterectomy or atherectomy. During such interventional procedures, there is a danger of breaking plaque free from the vessel walls. Filters are used to prevent plaque and other material which may be dislodged during such interventional procedures from traveling downstream where they can obstruct or restrict blood flow.

A filtering device is disclosed in WO 98/33443 which published Aug. 6, 1998 by inventor Jay Yadav which is hereby incorporated by reference. One of the filters disclosed in the published application at FIG. 9 shows a filter which is expanded with a single spiral structural wire attached to the filter. A fiber is attached to the spiral wire and tension is applied by the fiber to collapse the spiral wire. When tension on the fiber is released, the wire and attached filter expand.

The present invention is directed to improved methods and devices for filtering fluid flow in patients and, in particular, for filtering blood flow.

SUMMARY OF THE INVENTION

The filter device of the present invention has a filter element and an expandable element which expands the filter element. The filter element is preferably biased toward the collapsed position and the expandable element is preferably biased toward the expanded position. The expandable element is tensioned to hold the expandable element in the collapsed shape. Tension is released to permit the expandable element to expand the filter element. The proximal end of the filter element is preferably biased toward the collapsed position so that material trapped in the filter element cannot escape when the filter device is collapsed and removed.

The expandable element preferably slides against an interior surface of the filter element to expand the filter element. The sliding engagement between the filter element and expandable element permits the filter element to expand to various intermediate sizes for filtering varying size vessels. The sliding engagement between the filter element and the expandable element also permits the filter element and the expandable element to lengthen, distort, and rotate independently of one another which cannot occur with the filter device of WO 98/33443 described above.

The expandable element is preferably formed with less than three filaments and preferably only one filament. The filament advantageously can be collapsed to a diameter of less than 0.040 inch so that the filter device can access small, tortuous vessels. The filament preferably forms a coil in the expanded position which has an increasing diameter proximally to form a conical shape.

The filter element may be any suitable material such as an elastomeric membrane or a mesh structure. The filter element is attached to a core element and is collapsed around the core element and expandable element. The expandable element is preferably slidably coupled to the core element with a loop, interlocking connection or coaxial configuration.

These and other features and advantages of the invention will become apparent from the following description of the preferred embodiments, drawings and claims.

BRIEF DESCRIPTION OF THE DRAWINGS

FIG. 1 shows a filter device in a collapsed position.

FIG. 2 shows the filter device of FIG. 1 in an expanded position.

FIG. 5 shows the filter device having a mesh structure in a collapsed position.

FIG. 6 shows the filter device of FIG. 5 in an expanded position.

FIG. 9 shows another filter device in a collapsed position.

FIG. 10 shows the filter device of FIG. 9 in an expanded position.

DESCRIPTION OF THE SPECIFIC EMBODIMENTS

Figure 3:
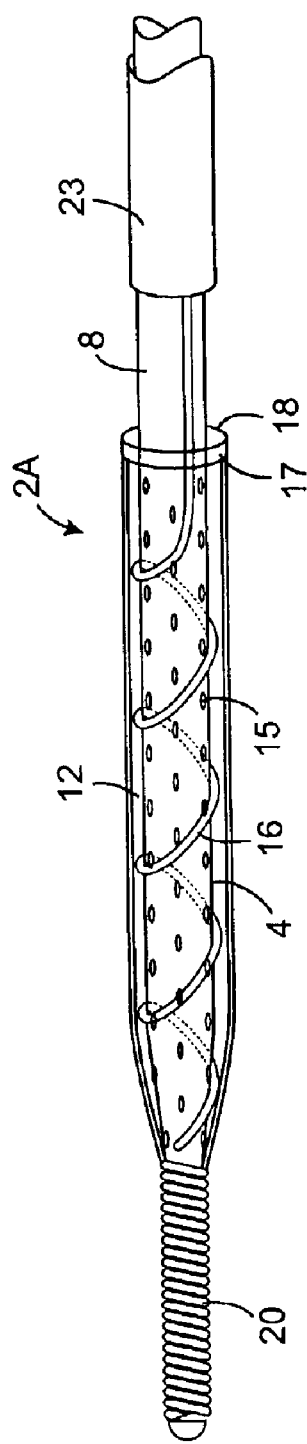
FIG. 3 shows another filter device in a collapsed position.

Referring to FIGS. 1 and 2, a filter device 2 for filtering fluid flow through a body passage, such as a blood vessel, is shown. The filter device 2 has a filter element 4 for filtering flow through the body structure and an expandable element 6 for moving the filter element 4 from the collapsed position of FIG. 1 to the expanded position of FIG. 2. The filter device 2 is advanced through the body passage in the collapsed position and expanded at the desired location to filter fluid flow through the body passage. The filter element 4 and expandable element 6 are both mounted to a core element 8. The device 2 is advanced through or into anatomical position by pushing the core element 8.

The filter element 4 is preferably biased toward the collapsed position and the expandable element 6 is preferably biased toward the expanded position. The expandable element 6 is held in the collapsed position by applying tension to collapse the expandable element 6 to the position of FIG. 1. The expandable element 6 is preferably wrapped around the core element 8 in the collapsed position so that the expandable element 6 and core element 8 do not rotate significantly relative to one another when the expandable element 6 expands. When the filter element 2 is ready to be deployed, tension on the expandable element 6 is released to, permit expansion of the expandable element 6. The expandable element 6 may also be advanced further to apply a compressive force to the expandable element 6 to further expand the expandable element 6.

The filter element 4 may be biased toward the collapsed position by providing the filter element 4 with elastic properties. The proximal end of the filter element 4 may also have a ring 17 around a proximal end 18 to hold the filter element 4 in the collapsed position and to ensure that the filter element 4 closes around any material trapped in the filter element 4 when removing the filter device 2. The ring 17 may simply be a thickened portion of the filter element 4, an additional layer dipped over the filter element 4 or a separate ring which is bonded to or woven into the filter element 4.

The filter element 4 may be any suitable material such as a membrane 12 or a mesh structure 14 (FIGS. 5 and 6). The membrane 12 may be made of a permeable material or an impermeable material with holes 15 therein to provide permeability. For example, the filter element 4 may be a CHRONOPRENE, which is a modified thermoplastic isoprene sold by CT Biomaterials, or silicone membrane with the holes 15 therein. The filter element preferably has an outer diameter of 0.025–0.080 inch and more preferably 0.025–0.038 inch. The proximal end of the filter element 4 preferably opens to a size of 6–12 mm.

The filter element 4 forms a permeable structure which filters unwanted material from the fluid flow and the size of the holes 15 is selected to remove the unwanted material while still permitting fluid flow through the body structure. The filter element 4 may be used, for example, to remove plaque and other emboli during interventional procedures in blood vessels. Use of the filter element 4 prevents plaque dislodged during the interventional procedure from traveling downstream where the plaque can restrict or obstruct blood flow.

Figure 8:
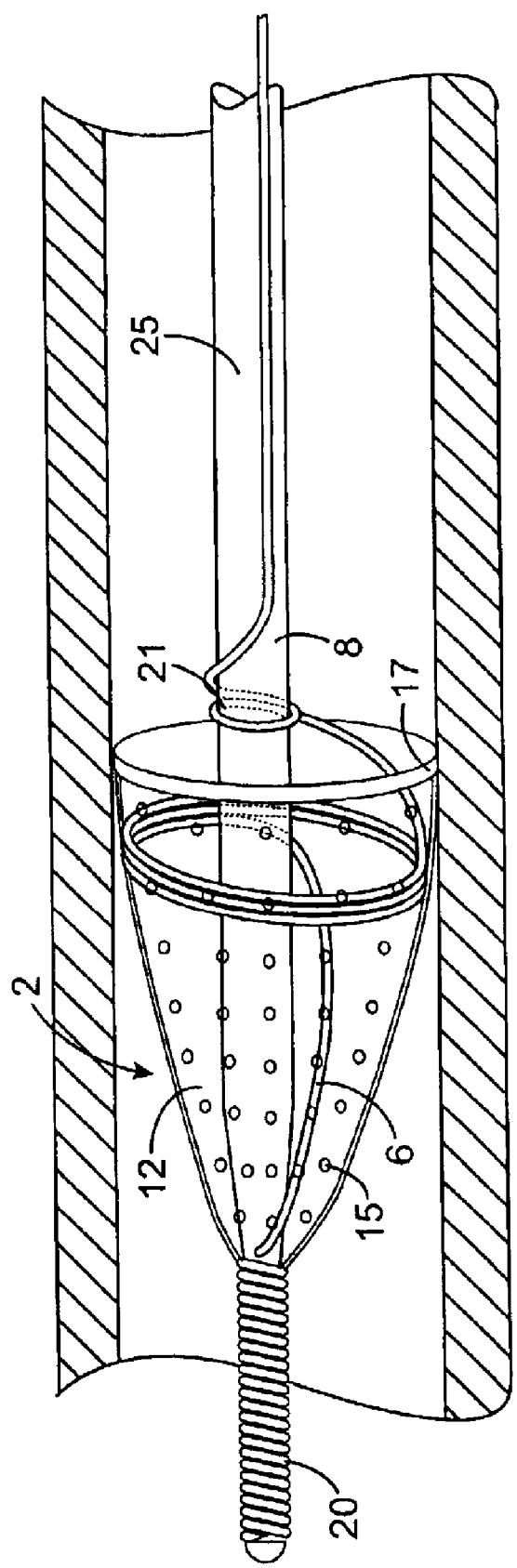
FIG. 8 shows the filter device having an expandable member with closely spaced coils.

The expandable element 6 preferably forms a coil 20 which increases in diameter proximally to form a conical shape. The expandable element 6 preferably forms at least 1–8 loops, more preferably 2–6 loops, and most preferably about 4 loops in the expanded position. The expandable element 6 may also take any other shape including spherical, dumbbell or any other geometry in the expanded position. Referring to FIG. 8, the expandable element 6 may have coils 20 which are positioned close to one another.

The expandable element 6 is preferably made of a superelastic material such as nitinol but may be made of any other suitable material. The expandable element 6 preferably has a thickness of 0.005–0.015 inch. The expandable element 6 may provide sufficient radiopacity or a radiopaque material may be coated, plated or sputtered onto the expandable element. The expandable element 6 may also have a hollow core which is filled with a radiopaque material such as gold or platinum. The expandable element 6 may have any cross-sectional shape such as round wire or rectangular ribbon. The expandable element 6 may also utilize shape memory characteristics with the expandable element 6 assuming the expanded shape when heated.

The expandable element 6 is preferably a single filament 16 but may also be two or three filaments which act together to open the filter element 4. An advantage of using a limited number of filaments 16, preferably only one, is that the expandable element 6 can be collapsed to a very small profile. In particular, the expandable element 6 preferably has a maximum diameter of no more than 0.040 inch, more preferably no more than 0.020 inch and most preferably no more than 0.015 inch when in the collapsed position for accessing small, tortuous vessels such as the cerebral vasculature. The expandable element 6 may, of course, take any other size depending upon the particular application. The distal end of the expandable element 6 is attached to the core element 8 by any suitable method such as soldering, welding, brazing or adhesive bonding.

As mentioned above, the filter element 6 and the expandable element 4 are both mounted to the core element 8 so that the expandable element 6 is free to displace relative to the filter element. As such, the expandable element 4 slides along an interior surface 19 of the filter element 6 when expanding the filter element 6. An advantage of permitting free movement between the expandable element 6 and the filter element 4 is that the expandable element 6 and filter element 6 may expand only as necessary to engage the walls of the passage. In this manner, the filter may assume various intermediate sizes for filtering flow through varying size vessels. Another advantage is that the filter element 4 and expandable element 6 may distort, elongate and/or unwind independently. The filter element 4 may be coupled to the expandable element 6 at one or more locations without departing from the scope of the invention, however, the expandable element 6 is preferably not attached to the filter element 4. Specifically, the expandable element 6 is preferably free to move and is not attached to the filter element 6 at any locations proximal to the distal end of the filter element 4. The expandable element 6 has a loop 21 which extends around the core element 8 so that the expandable element 6 is slidably coupled to the core element 8. The expandable element 6 may be coupled to the core element 8 in any other manner such as an interlocking or coaxial configuration.

The core element 8 may be made of any suitable materials and is preferably stainless steel or nitinol. The core element 8 is preferably tapered distally and has a diameter of less than about 0.026 inch, more preferably less than 0.014 inch and most preferably about 0.008–0.012 inch at a distal portion 25. The core element 8 preferably tapers up toward the proximal end to a diameter of about 0.035 inch. The core element 8 provides column strength and pushability so that the filter device 2 can be advanced to the desired location. When the filter device 2 is used in the vascular system, the filter device 2 may be advanced through a microcatheter, balloon catheter (not shown) or the like. The core element 8 may have a platinum or stainless steel coil 20 at the distal end to provide a soft, atraumatic tip and provide fluoroscopic visibility. The coil 20 is preferably 0.002–0.010 inch diameter wire and preferably extends 2–20 cm. The coil 20 is wound to a diameter of 0.018–0.038 inch.

Figure 7:
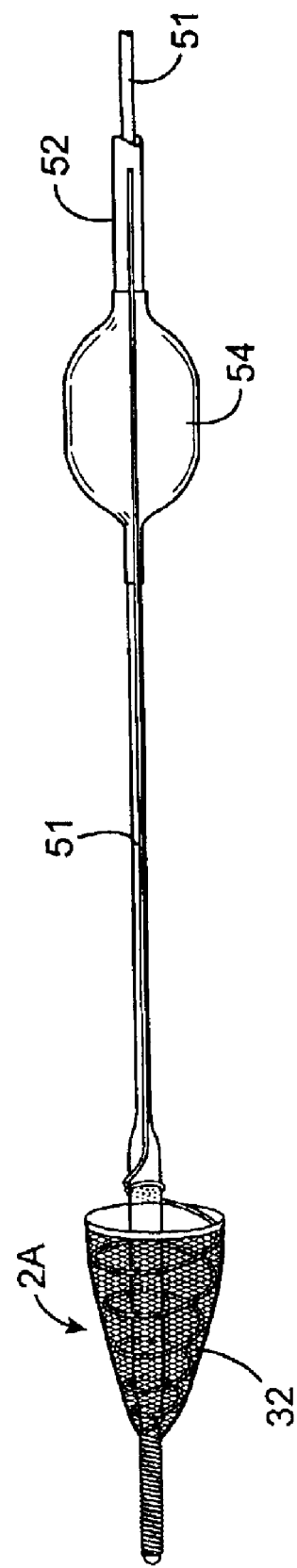
FIG. 7 shows a balloon catheter advanced over the filter device.

Referring to FIG. 7, a balloon catheter 52 having a balloon 54 is advanced over the core element 8. The balloon 54 may be used to open a narrowed portion of a vessel or may be used to block fluid flow through the body passage during deployment and/or retrieval of the filter element 32. A stiffening element (not shown) may be positioned over the proximal section 51 during advancement to provide column strength to the proximal section 51 of the core element 8. A distal portion of the core element 8 may have a larger cross-sectional size than a proximal portion to support the filter element 6 and to resist buckling of the core element 8 when tension is applied to the expandable element 6.

Figure 4:
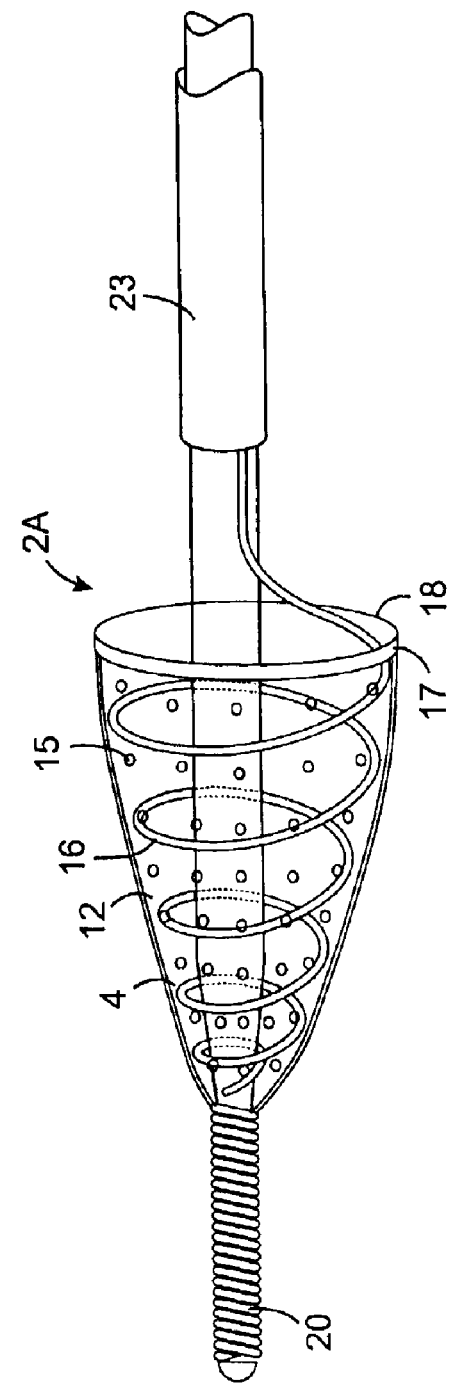
FIG. 4 shows the filter device of FIG. 3 in an expanded position.

Referring to FIGS. 3 and 4, another filter device 2A is shown wherein the same or similar reference numbers refer to the same or similar structure. A filter element 32 is attached to the core element 8 and the expandable element 6 is attached to a sleeve 23 which extends around the core element 8. The sleeve 23 is pulled to tension and collapse the expandable element 6 and is advanced to reduce tension to permit the expandable element 6 to expand. The sleeve 23 may also be advanced further to compress the expandable element 6 for further expansion. The filter device 2A is used in substantially the same manner as the filter device 2.

Referring to FIGS. 9 and 10, another filter device 2B is shown wherein the same or similar reference numbers refer to the same or similar structure. The device 2B has the expandable element 6 which is contained within a sheath 60. The expandable element 6 is held in a collapsed position by the sheath 60. A filter element 62, which may be any of the filter elements described above or any other suitable filter element, has a proximal end 64 which is positioned around the sheath 60. The filter element 62 is biased toward the collapsed position and may have the ring 17 to hold the filter element 62 in the collapsed position. The filter device 2B is advanced into position in the collapsed position. When the filter is ready to be deployed, the sheath 60 may be retracted or the expandable element 6 may be advanced so that the coils 60 are free to expand the filter element 62.

While the above is a complete description of the preferred embodiments of the invention, various alternatives, substitutions and modifications may be made without departing from the scope thereof, which is defined by the following claims. For example, the filter device may take on other shapes and sizes and the filter device may be used in any part of the body other than the vascular system. Furthermore, although the filter devices are described in connection with filtering fluid flow, the various mechanisms for deploying the filters may be used for occluding devices rather than filtering devices. Thus, the mechanical actuating mechanisms for actuating the filters may be used for actuating occluding structures without departing from the scope of the invention.

What is claimed is:

1. A device for intravascular use, comprising:

a wire;

a core element; and an expandable element, the expandable element being movable between a collapsed position and an expanded position, the expandable element being naturally biased toward the collapsed position, the wire also having a collapsed shape and an expanded shape, the wire being tensioned to hold the wire in the collapsed shape, the expandable element being mounted to the core element;

the wire being wrapped around the core element and being advanceable into the expandable element so that the wire expands the expandable element toward the expanded position, the wire sliding against an interior surface of the expandable element and being free to move relative to the expandable element at all locations proximal to a distal end.

2. The device of claim 1, wherein:

the wire forms coils in the expanded position.

3. The device of claim 1, wherein:

the wire may be compressed when expanding the expandable element.

4. The device of claim 1, wherein:

the expandable element is a mesh.

5. An intravascular device, comprising of:

a wire;

a core element; and an expandable element mounted to the core element and being movable between a collapsed position and an expanded position, the expandable element being naturally biased toward the collapsed position;

the wire also having a collapsed shape and an expanded shape, the wire being tensioned to hold the wire in the collapsed shape, wherein releasing at least some tension on the wire permits the wire to expand toward the expanded position thereby expanding the expandable element, the wire sliding against an interior surface of the expandable element and being free to move relative to the expandable element at all locations proximal to a distal end, the wire being wrapped around the core element.

6. The device of claim 5, wherein:

the wire forms coils in the expanded position.

7. The device of claim 5, wherein:

the wire may be compressed to further expand the expandable element after releasing all of the tension on the wire.

8. The device of claim 5, wherein:

the expandable element is a mesh.

* * * * *